US00PP12973P2

(12) United States Plant Patent
Osiecki

(10) Patent No.: US PP12,973 P2
(45) Date of Patent: Sep. 17, 2002

(54) AGLAONEMA PLANT NAMED 'SILVER MOON'

(75) Inventor: Marian W. Osiecki, Marianna, FL (US)

(73) Assignee: Oglesby International, Inc., Aetha, FL (US)

( * ) Notice: Subject to any disclaimer, the term of this patent is extended or adjusted under 35 U.S.C. 154(b) by 39 days.

(21) Appl. No.: 09/801,596

(22) Filed: Mar. 9, 2001

(51) Int. Cl.[7] ..... A01H 5/00

(52) U.S. Cl. ..... Plt./376
(58) Field of Search ..... Plt./376

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Aglaonema plant named 'Silver Moon', characterized by its symmetrical, round, relatively compact, full and dense plant form; freely branching habit; relatively thick stems and short internodes; broad leaves with obtuse bases and short petioles; bi-colored leaves with a silver green central zone and a dark green marginal zone.

2 Drawing Sheets

BACKGROUND OF THE INVENTION

The present Invention relates to a new and distinct cultivar of Aglaonema plant, botanically known as Aglaonema hybrid, and hereinafter referred to by the name 'Silver Moon'.

The new cultivar is a product of a planned and controlled breeding program conducted by the Inventor in Altha, Fla. The objective of the breeding program is to create compact and full Aglaonema cultivars with attractive leaf coloration and patterns.

The new cultivar originated from a self-pollination made by the Inventor of the Aglaonema hybrid 'Silver Bay', not patented. The cultivar Silver Moon was discovered and selected by the Inventor as a plant within the resulting progeny from the self-pollination in a controlled environment in Altha, Fla., in October, 1994.

Asexual propagation of the new cultivar by cuttings in Altha, Fla., since 1995, has shown that the unique features of this new Aglaonema plant are stable and reproduced true to type in successive generations of asexual propagation.

SUMMARY OF THE INVENTION

The new Aglaonema has not been observed under all possible environmental conditions. The phenotype may vary somewhat with variations in environment such as temperature, light intensity, fertilizer rate, irrigation amount and frequency, and/or propagation procedures without, however, any variance in genotype.

The following traits have been repeatedly observed and are determined to be the unique characteristics of 'Silver Moon'. These characteristics in combination distinguish 'Silver Moon' as a new and distinct cultivar:

1. Plants of the new Aglaonema are symmetrical, round in shape, relatively compact, full and dense, and are suitable for 15 to 25-cm containers.
2. Plants of the new Aglaonema are freely branching.
3. Plants of the new Aglaonema have relatively thick stems and short internodes.
4. Leaves of plants of the new Aglaonema are broad with obtuse bases and have short petioles.

5. Leaves of the new Aglaonema are bi-colored with a silver green central zone and a dark green marginal zone.

Plants of the new Aglaonema differ from plants of the parent, the cultivar Silver Bay, in the following characteristics:

1. Plants of the new Aglaonema are shorter and slightly more upright than plants of the cultivar Silver Bay.
2. Plants of the new Aglaonema have shorter internodes than plants of the cultivar Silver Bay.
3. Plants of the new Aglaonema have smaller leaves than plants of the cultivar Silver Bay. In addition, leaf bases of plants of the new Aglaonema are obtuse whereas leaf bases of plants of the cultivar Silver Bay are cuneate.
4. Plants of the new Aglaonema have shorter petioles than plants of the cultivar Silver Bay.
5. Leaves of plants of the new Aglaonema are bi-colored whereas leaves of plants of the cultivar Silver Bay are tri-colored.
6. Plants of the new Aglaonema have smaller spathes and spadices than plants of the cultivar Silver Bay.

Plants of the new Aglaonema can be compared to the Aglaonema cultivar Rhapsody in Green, disclosed in U.S. Plant Pat. No. 8,975. However, in side-by-side comparisons conducted in Altha, Fla., plants of the new Aglaonema differ from plants of the cultivar Rhapsody in Green in the following characteristics:

1. Plants of the new Aglaonema are shorter, more rounded, more compact, and fuller than plants of the cultivar Rhapsody in Green.
2. Plants of the new Aglaonema have shorter internodes than plants of the cultivar Rhapsody in Green.
3. Plants of the new Aglaonema have thicker stems than plants of the cultivar Rhapsody in Green.
4. Plants of the new Aglaonema have broader leaves than plants of the cultivar Rhapsody in Green. In addition, leaf bases of plants of the new Aglaonema are obtuse whereas leaf bases of plants of the cultivar Rhapsody in Green are cuneate.
5. Leaves of plants of the new Aglaonema have shorter and thicker petioles than leaves of plants of the cultivar Rhapsody in Green.

6 Leaves of plants of the new Aglaonema have a more striking bi-colored contrast than leaves of plants of the cultivar Rhapsody in Green; that is, the central zone of leaves of the new Aglaonema is more silver gray and the marginal zone is darker green than leaves of the cultivar Rhapsody in Green.

Plants of the new Aglaonema can also be compared to the Aglaonema cultivar Deborah, disclosed in U.S. Plant Pat. No. 9,775. However, in side-by-side comparisons conducted in Altha, Fla., plants of the new Aglaonema differ from plants of the cultivar Deborah in the following characteristics:

1. Plants of the new Aglaonema are shorter, more rounded, more compact, and fuller than plants of the cultivar Deborah.
2. Plants of the new Aglaonema have shorter internodes than plants of the cultivar Deborah.
3. Plants of the new Aglaonema have green-colored stems whereas plants of the cultivar Deborah have white-colored stems.
4. Plants of the new Aglaonema have slightly shorter and broader leaves than plants of the cultivar Deborah.
5. Leaves of plants of the new Aglaonema have shorter petioles than leaves of plant of the cultivar Deborah. In addition, leaf petioles of plants of the new Aglaonema are green in color whereas leaf petioles of plants of the cultivar Deborah are white in color.
6. Leaves of plants of the new Aglaonema are bi-colored whereas leaves of plants of the cultivar Deborah are multicolor and mottled with a contrasting white midrib.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Aglaonema.

The photograph on the first sheet comprises a side perspective view of a typical plant of 'Silver Moon' in a 25-cm container about 14 months after planting a single rooted cutting that was about 15-cm tall.

The photographs on the second sheet comprise close-up views of the upper (top photograph) and lower (bottom photograph) surfaces of typical leaves of 'Silver Moon'.

DETAILED BOTANICAL DESCRIPTION

The following observations and measurements were recorded on plants grown in Homestead, Fla., in polypropylene-covered shadehouses and under conditions which closely approximate those used in commercial horticultural practice. The polypropylene shadecloth provided light reduction of 73% of the ambient light level. During the production of these plants, day temperatures ranged from 18 to 41° C., night temperatures ranged fromn 15 to 32° C., and light level ranged from 800 to 2,500 foot-candles. Plants used for this description were grown as single plants in 25-cm containers and were about 14 months from planting a rooted cutting that was about 15 cm tall. Fully developed plant structures and organs were used for the following observations and measurements unless otherwise indicated.

In the following description, color references are made to The Royal Horticultural Society Colour Chart except where general terms of ordinary dictionary significance are used. Numerical measurements represent averages from typical plants of 'Silver Moon'.

Botanical classification: Aglaonema hybrid cultivar Silver Moon.

Parentage: Self-pollination of Aglaonema hybrid cultivar Silver Bay, not patented.

Propagation:

*Type.*—By cuttings.

*Time to develop roots.*—Summer: About 21 days at 32° C. Winter: About 35 days at 21° C.

*Root description.*—Relatively thick, freely branching and cream-colored.

Plant description:

*Growth habit.*—Symmetrical and rounded plant form; relatively compact, full and dense. Freely branching. Appropriate for 15 to 25-cm containers.

*Plant height.*—About 46.4 cm.

*Plant diameter* (*area of spread*).—About 70.6 cm.

*Plant vigor.*—Vigorous.

*Crop time.*—About 12 to 14 months are required to produce a finished plant in a 25-cm container from a single rooted cutting, that is about 10 to 15-cm tall.

*Stem description.*—Diameter: About 2.4 cm. Internode length: About 1 cm. Color: Close to 147A or darker than 147A. Stems are not visible due to the clasping nature of the petiole sheaths.

*Leaf description.*—Shape: Elliptic, asymmetrical. Apex: Acuminate with some aristate tendencies. Base: Obtuse. Margin: Entire. Length, mature leaves: About 28.6 cm. Width, mature leaves: About 11.2 cm. Length to width ratio, mature leaves: About 2.6 to 1. Aspect: When first unrolled, about 30 to 40° from stem axis; with development, to 55 to 75° from stem axis. Surface: Slightly wavy. Texture: Relatively thick. Color: Young leaves, just after unfurling, upper surface: Bi-colored with two contrasting color zones. Central silver green (191B) zone about 5 to 6 cm wide at mid-leaf; surrounded by marginal dark green (varies between different combinations of 137A, 146A, 147A and a color darker than 144A) zone, about 1.5 to 2.5 cm wide at mid-leaf. The edge between the two zones is irregular yet clearly defined. Few small isolated blotches of green, similar in color to the marginal zone, are present in the central zone, usually near to the marginal zone. Fewer small blotches of silver green, similar in color to the central zone, are present in the marginal zone, near the central zone. Primary veins are similar in color to the surrounding tissue. Leaves, glossy. Young leaves, just after unfurling, lower surface: Between 146B and 147B. Proximal portion of midrib, close to 146C. Primary veins darker than the surrounding tissue, between 147B and 147A. Mature leaves, upper surface: Bi-colored with two contrasting color zones. Central silver green (more silver gray and slightly darker than 191A) zone about 6 to 7 cm wide at mid-leaf; surrounded by marginal dark green (much darker than 147A) zone, about 2 to 3 cm wide at mid-leaf. The edge between the two zones is irregular yet clearly defined. Few small isolated blotches of dark green, similar in color to the marginal zone, are present in the central zone, usually near to the marginal zone. Fewer small blotches of silver green, similar in color to the central zone, are present in the marginal zone, near the central zone. Primary veins are similar in color to the surrounding tissue. Midrib very similar to or slightly darker and greener than the surrounding tissue in the central zone. Primary veins, similar in color as surrounding tissue, close to 147A. Leaves, glossy. Mature leaves, lower surface: Between 147B and 146A. Midrib close to 146B; primary veins darker than the surrounding tissue, close to 147A.

*Petiole.*—Length, primary shoot: About 13.6 cm. Diameter, primary shoot, at leaf blade junction: About 5.6 mm. Diameter, at wing apex: About 6.3 mm. Wing length: About 11.2 cm. Wing width, mid-section: About 8 mm. Color: Young leaves, just after leaf unfurling: Close to 146C. Mature leaves, winged area: Adaxial, between 146C and 146D; abaxial, 147B near leaf blade junction, proximally lighter, 147C. Mature leaves, above winged area: Between 147B and 147C. Mature leaves, wings: Adaxial, between 146B and 146C; abaxial, 146A near petiole, lighter towards margins, 146C.

Inflorescence description:

*Arrangement.*—Spathes with spadices held relatively strong peduncles. Flowering structures arise from leaf axils. About 4 to 5 inflorescences per floral sympodium. Spathes on short peduncles subtended by petiole base of a leaf which is smaller than other mature leaves. Peduncles thick, usually slightly bent and outwardly spreading. Spathes generally in alignment with the peduncle.

*Time to flowering.*—About 12 to 16 months from planting a rooted cutting.

*Inflorescence longevity.*—Spathes last about 8 to 10 weeks after opening.

*Fragrance.*—Not detected.

*Spathe.*—Shape: Spathes are usually closed and are open for slightly more than one day when stigmas are receptive. When open, spathes are boat-shaped with aristate apices; margin, entire. Spadix is positioned about 20° beyond the spathe axis. Length: About 7.7 cm. Width: About 1.9 cm. Length to width ratio: About 4.1 to 1. Color: Frontal surface: Lighter than 146D. Rear surface: Between 146C and 146D; midrib, 146A to 146B.

*Spadix.*—Shape: Columnar, tapering towards the apex. At base, zone with few, about 8 to 13, single female flowers; zone above with numerous male flowers. Spadix length: About 4.2 cm. Length of female zone: About 8 cm. Length of male zone: About 3.9 cm. Diameter of female zone: About 9.5 mm. Diameter of male zone: About 7.2 mm. Color: Female zone: Stigmas, between 160A and 160B; styles and ovaries vary between 158A, 158B and 158C. Male zone, before pollen dehiscence: Varies between 158A, 158B and 158C. Pollen, cream-white.

*Seed.*—Female flowers develop into berries that are ovoid with flat apices. One seed per fruit; seeds, between ellipsoid and ovoid in shape.

*Color.*—Brown.

*Peduncle.*—Length: About 9.4 cm. Diameter: About 5.1 by 6 mm. Stipe length: About 1.2 mm. Color: 146A or slightly darker than 146A.

Disease/insect resistance: Plants of the new Aglaonema grown in commercial greenhouses have not shown any unusual susceptibility to pathogens or insects common to Aglaonema.

Low temperature tolerance: Plants of the new Aglaonema have been observed to tolerate temperatures as low as 12° C.

It is claimed:

1. A new and distinct cultivar of Aglaonema plant named 'Silver Moon', as illustrated and described.

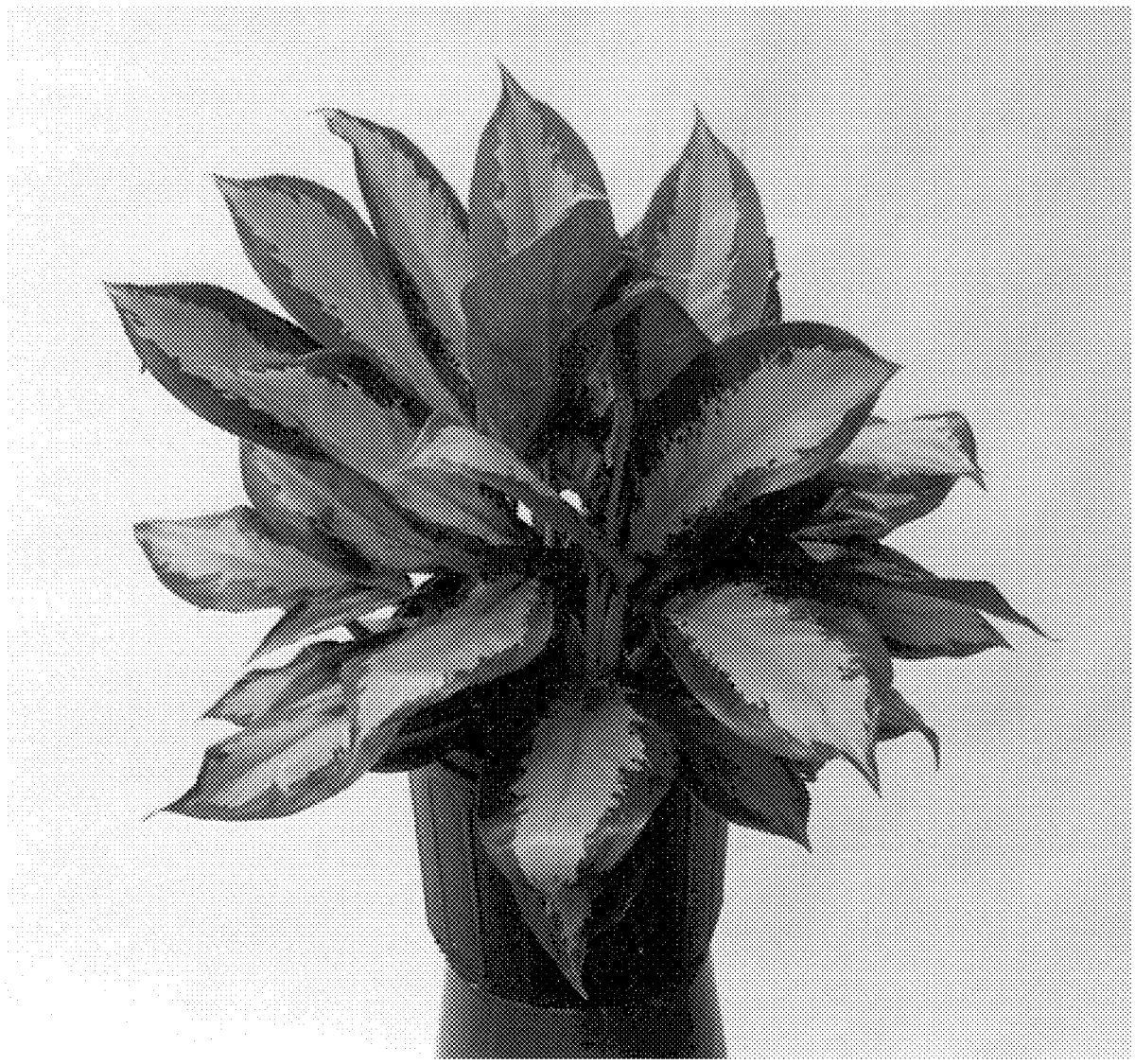

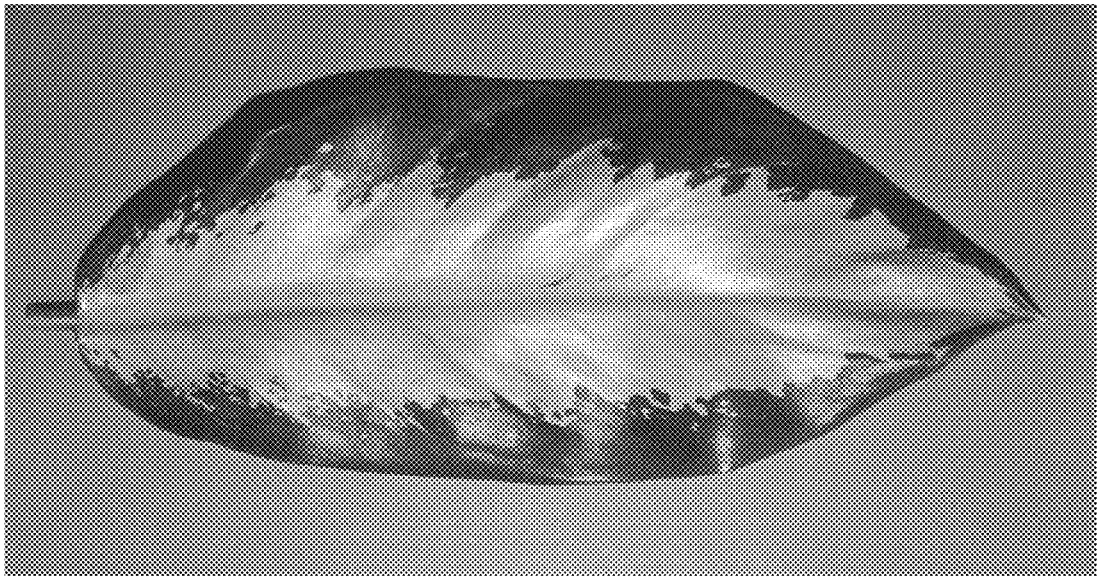
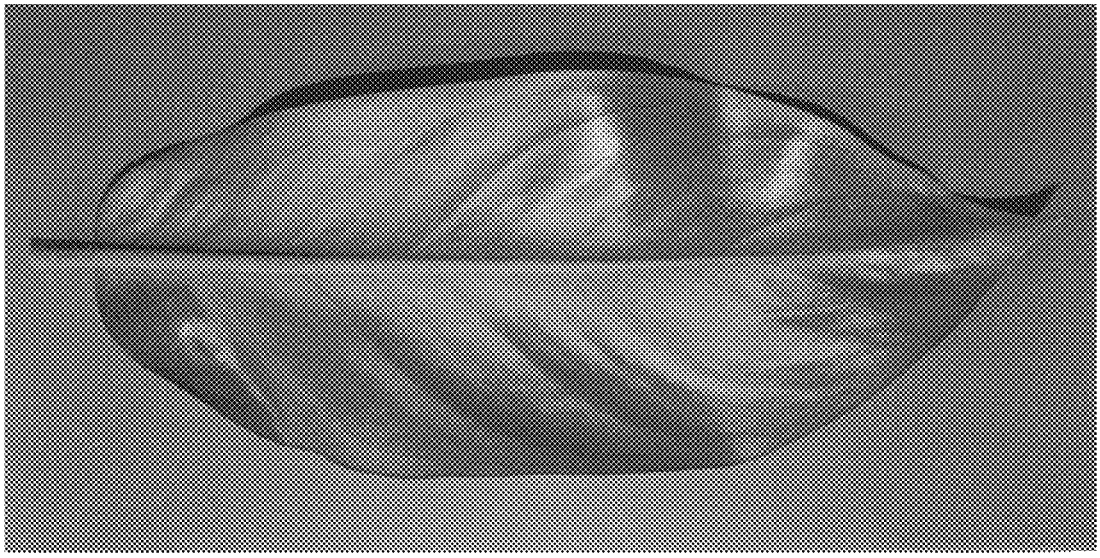

* * * * *